(12) United States Patent
Choi et al.

(10) Patent No.: US 10,048,260 B2
(45) Date of Patent: Aug. 14, 2018

(54) PS-SPCL SEARCHING APPARATUS AND METHOD USING SURFACE PLASMON RESONANCE

(71) Applicant: Electronics and Telecommunications Research Institute, Daejeon (KR)

(72) Inventors: Yo Han Choi, Daejeon (KR); Moon Youn Jung, Daejeon (KR); Seon Hee Park, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 1190 days.

(21) Appl. No.: 14/073,653

(22) Filed: Nov. 6, 2013

(65) Prior Publication Data

US 2014/0066331 A1 Mar. 6, 2014

Related U.S. Application Data

(62) Division of application No. 12/746,992, filed as application No. PCT/KR2008/002162 on Apr. 17, 2008, now abandoned.

(30) Foreign Application Priority Data

Dec. 12, 2007 (KR) .......................... 10-2007-0128989

(51) Int. Cl.
G01N 21/552 (2014.01)
G01N 33/543 (2006.01)
C40B 30/00 (2006.01)

(52) U.S. Cl.
CPC ....... *G01N 33/54373* (2013.01); *C40B 30/00* (2013.01); *G01N 21/553* (2013.01)

(58) Field of Classification Search
None
See application file for complete search history.

(56) References Cited

U.S. PATENT DOCUMENTS

2005/0123902 A1* 6/2005 Meneses ................ A61K 31/41
435/5

FOREIGN PATENT DOCUMENTS

KR 1020030025787 A 3/2003
WO WO 96/09547 A2 3/1996

OTHER PUBLICATIONS

Wegner et al (2004 Anal Chem 76:5677-84).*
Pedersen et al (2004 Opt. Eng. 43:2505-10).*
Reineke et al (2002 J. Immunological Methods 267:37-51).*
Chang-Sub Park et al., "The polymer waveguide type SPR sensor using a multi-wavelength light source," Journal of Korean Sensors Society, 2007, pp. 401-406, vol. 16, No. 6.
Benjamin T. Houseman, "Peptide chips for the quantitative evaluation of protein kinase activity," Nature Biotechnology, Mar. 2002, pp. 270-274, vol. 20, Nature Publishing Group.
International Search Report for PCT/KR2008/002162 filed Apr. 17, 2008.
Written Opinion of the International Searching Authority for PCT/KR2008/002162 filed Apr. 17, 2008.

* cited by examiner

*Primary Examiner* — Christopher M Gross

(57) ABSTRACT

A Positional Scanning-Synthetic Peptide Combinatorial Library (PS-SPC) searching apparatus and method using Surface Plasmon Resonance (SPR) are provided. The method includes spotting and fixing each of a plurality of peptide pools to a top of one thin metal film, inputting specific materials to the top of the thin metal film, applying a TM-mode light to a bottom of the thin metal film and exciting SPR for the thin metal film, and detecting a TM mode reflected light reflected from the thin metal film and displaying the detected light as a two-dimensional image.

10 Claims, 6 Drawing Sheets

[Fig. 2]
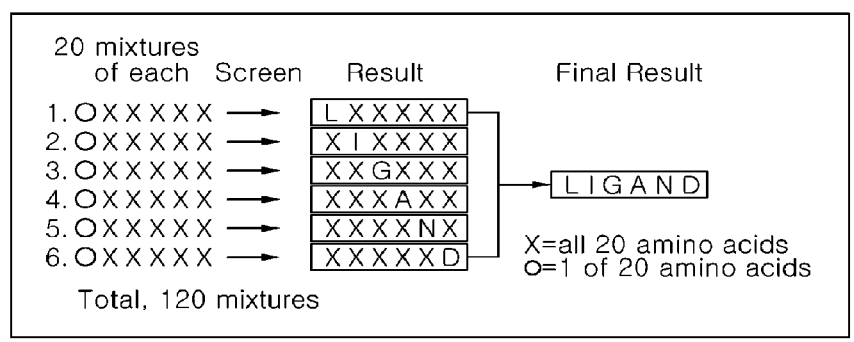

[Fig. 3]
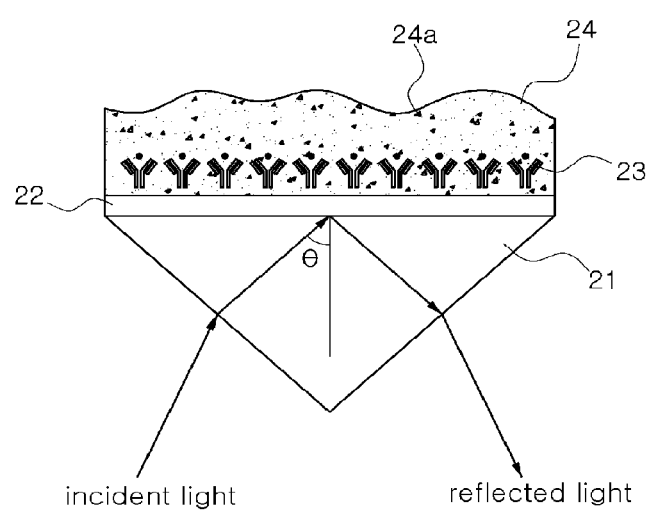

[Fig. 4]
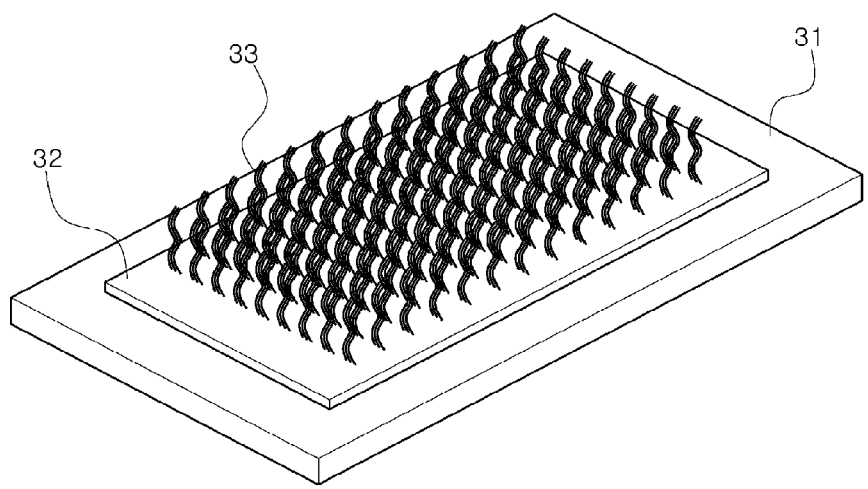

[Fig. 5]
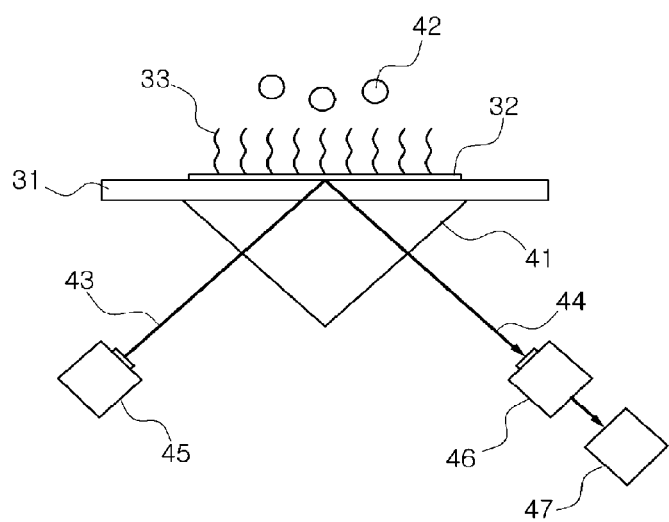

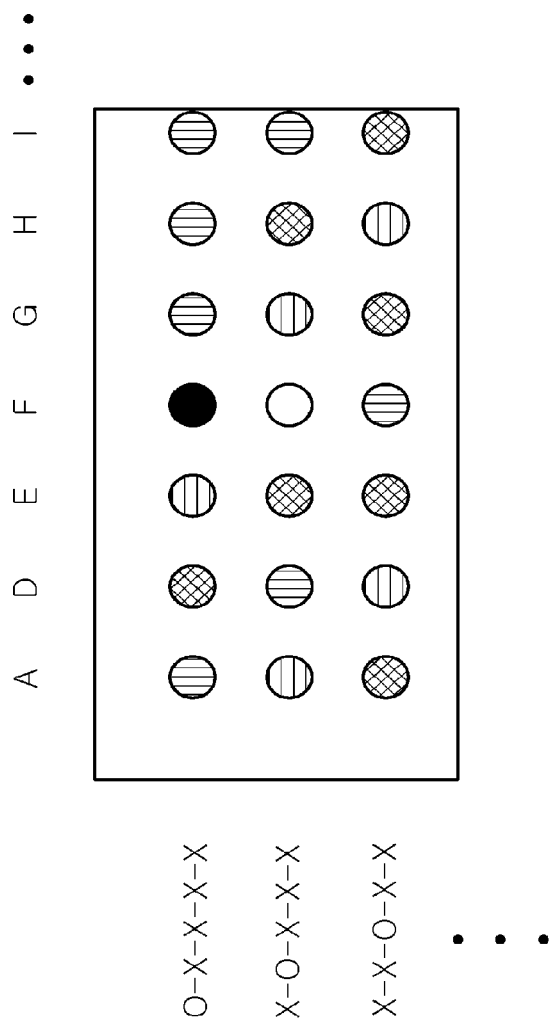

PS-SPCL SEARCHING APPARATUS AND METHOD USING SURFACE PLASMON RESONANCE

TECHNICAL FIELD

The present invention relates to an apparatus for searching a molecular reaction using Positional Scanning-Synthetic Peptide Combinatorial Library (PS-SPCL) that is a kind of peptide library. More particularly, the present invention relates to a PS-SPCL searching apparatus and method using Surface Plasmon Resonance (SPR), for displaying the PS-SPCL searching result as an image using SPR.

The invention has been supported by ITR&D Program of MIC/IITA [2006-S-007-02, Ubiquitous Health Monitoring Module and System Development].

BACKGROUND ART

Peptide library refers to a combination of hundreds to thousands of peptides, a combination and sequence of which are arbitrarily varied using combinatorial chemistry. The peptide library is used for the development of a potential preliminary new medicine (a lead compound) having a biological activity.

PS-SPCL is a kind of peptide library. The PS-SPCL is a combination of mixtures that are prepared in a way of fixing one of 19 amino acids (except cysteine) in a specific position and connecting mixtures of the 19 amino acids in remaining positions. The PS-SPCL is used for the development of new peptide hormone materials, the definition of antibody epitopes, and the development of antimicrobial, antibiotics, enzyme detergent, and physiological active peptide.

FIG. 1 is a schematic diagram illustrating a scheme of PS-SPCL. As shown in FIG. 1, in mixtures of the first group of the PS-SPCL, different specific amino acids each are fixed in first positions and random amino acids are placed in remaining positions at the same rate. In mixtures of the second group, different specific amino acids each are fixed in second positions and random amino acids are positioned in remaining positions at the same rate. Also, in mixtures of the third group, different specific amino acids each are fixed in third positions and random amino acids are placed in remaining positions. In the above, a peptide synthesis process controls positioning specific amino acids in specific positions only and positioning random amino acids in remaining positions.

Thus, the PC-SPCL is composed of a plurality of peptide pools in which different specific amino acid is fixed in each sequence position.

For example, if pentamer PS-SPCL is made from 20 amino acids, 20 5=100 different peptide pools become one set.

The completed set is, as shown in FIG. 2, used to perform a screening process suitable to each purpose such as a reaction with specific materials or influence on enzyme. As a result, obtained is the result as to whether the most desired effect is obtained when any amino acids are positioned in first positions and also, whether it is most effective that any amino acids are positioned in second and third positions. In generalization, a linear peptide sequence that is a disclosure of an optimal amino acid by position is secured.

However, the PS-SPCL used in this process consumes a long time and many efforts and costs in its manufacturing because of its characteristic, but the PS-SPCL becomes extinct and cannot be used after once use.

Particularly, because the screening process is performed sequentially, it takes a few days to a few weeks to obtain a result though there is somewhat a difference depending on target materials.

As described above, the conventional art has a drawback in that it takes a long time and makes many efforts to search new materials using PS-SPCL and it continuously consumes the high-priced peptide library in view of the characteristic of the PS-SPCL.

DISCLOSURE OF INVENTION

Technical Problem

The present invention has been made to solve the foregoing problems with the prior art, and therefore the present invention provides a PS-SPCL searching apparatus and method using SPR, for displaying the result of PS-SPCL searching as an image using SPR, thereby greatly reducing a searching time and efforts made.

Technical Solution

According to an aspect of the present invention, a Positional Scanning-Synthetic Peptide Combinatorial Library (PS-SPCL) searching method using Surface Plasmon Resonance (SPR) is provided. The method includes spotting and fixing each of a plurality of peptide pools to a top of one thin metal film; inputting specific materials to the top of the thin metal film; applying a Transverse Magnetic (TM) mode light to a bottom of the thin metal film and exciting SPR for the thin metal film; and detecting a TM mode reflected light reflected from the thin metal film and displaying the detected light as a two-dimensional image.

In spotting and fixing each of the plurality of peptide pools to the top of the thin metal film, the plurality of peptide pools may be fixed to the surface of the thin metal by a covalent bond.

The thin metal film may be a metal emitting electron by an external stimulus and having a negative dielectric constant.

The method may further include, before spotting and fixing each of the plurality of peptide pools to the top of the thin metal film, synthesizing the plurality of peptide pools so that peptides come in contact with the surface of the thin metal film while forming a covalent bond by manipulating N-terminals or C-terminals of the peptides.

The method may further include detecting optimal amino acids by position from the two-dimensional image.

According to another aspect of the present invention, a Positional Scanning-Synthetic Peptide Combinatorial Library (PS-SPC) searching apparatus using Surface Plasmon Resonance (SPR) is provided. The apparatus includes a PS-SPCL chip including a thin metal film and a flat type transparent dielectric substrate for supporting the thin metal film, an incident light provision unit, a prism, and a reflected light detector. The thin metal film spots and fixes one or more peptide pools. The flat type transparent dielectric substrate supports the thin metal film. The incident light provision unit provides a TM mode incident light for exciting SPR. The prism propagates the incident light, which is provided by the incident light provision unit, from a bottom of the PS-SPCL chip to an interface between the thin metal film and the flat type transparent dielectric substrate and emits a reflected light reflected from the thin metal film. The reflected light detector detects a reflected light emitted through the prism and displays the detected light as a two-dimensional image.

The thin metal film may be a metal emitting electron by an external stimulus and having a negative dielectric constant.

The flat type transparent dielectric substrate may be formed of high refractive-index polymer materials comprising slide glass or CycloOlefin Copolymer (COC).

The apparatus may further include a signal processor for analyzing the two-dimensional image displayed by the reflected light detector and detecting optimal amino acids by position as amino acids that are fixed to peptide pools appearing most bright on the two-dimensional image among a peptide pool group whose different amino acids are fixed in the same position.

Advantageous Effects

As set forth above, the present invention has an excellent effect of enabling observations of the degree of each reaction between peptide pools and target materials, which induces a change of an SPR condition, at a time by fixing all of a set of peptide pools to a thin metal film in a constant array, then making the target materials flow to the thin metal film to induce the reaction between the peptide pools and the target materials, then making light incident on the thin metal film and exciting SPR, and then processing a reflected light reflected from the thin metal film into a two-dimensional image. Also, the present invention has an excellent effect of enabling the reuse of the thin metal film to which a plurality of the peptides pools are fixed, by removing only the target materials by a physiochemical method.

BRIEF DESCRIPTION OF THE DRAWINGS

FIG. 1 is a diagram illustrating an example of PS-SPCL;

FIG. 2 is a diagram illustrating an example of a conventional searching process using PS-SPCL;

FIG. 3 is a schematic diagram illustrating a basic construction of an SPR sensor;

FIG. 4 is a mimetic diagram illustrating a PS-SPCL chip according to an exemplary embodiment of the present invention;

FIG. 5 is a diagram illustrating the entire construction of a PS-SPCL searching apparatus using SPR according to an exemplary embodiment of the present invention; and FIG. 6 is a view showing an example of a two-dimensional image showing the result of PS-SPCL searching using SPR according to an exemplary embodiment of the present invention.

BEST MODE FOR CARRYING OUT THE INVENTION

Preferred embodiments of the present invention will be described herein below with reference to the accompanying drawings. In the following description, well-known functions or constructions are not described in detail since they would obscure the invention in unnecessary detail.

Throughout the drawings, it should be noted that like reference numbers are used to depict the same or similar elements, features and structures.

Throughout the specification, 'connecting of any part with other part' includes not only 'directly connecting' but also 'indirectly connecting' with another element interposed between them. 'Including any element' signifies not excluding other element but being able to further include other element unless otherwise indicated.

In searching new materials using PS-SPCL, the present invention is to divide a set of peptide pools of PS-SPCL on a group basis, then spot and fix the peptide pools to a surface of a thin metal film supporting surface plasmon, and then input target materials to the surface of the thin metal film, thereby enabling observations of an interaction between molecules, which are made in each peptide pool, through an SPR imaging technique. The present invention is to enable observations of the reaction of the set of peptide pools at a time and search for optimal reaction materials to target materials easily and simply, by making observations of a two-dimensional image obtained through the SPR imaging technique.

In order to help understanding of the present invention, a brief description of an SPR sensor is first made below.

FIG. 3 is a schematic diagram illustrating a basic principle of the SPR sensor.

Referring to FIG. 3, in the SPR sensor, if a Transverse Magnetic (TM) polarized light is incident on a thin metal film 22 through a prism 21, SPR takes place at specific incidence angle and thickness of the thin metal film 22. At this time, a phenomenon in which the energy of the incident light is absorbed into the thin metal film 22 and thus, induces a sudden decrease of the intensity of a reflected light reflected from the thin metal film 22 occurs.

The SPR is influenced by an incident angle and an effective thickness of the thin metal film 22. Therefore, target materials 24*a* contained in a sample 24 are coupled with fixed biomaterials 23 and thus a change of an effective thickness is induced, provided that with the incident angle fixed, the biomaterials 23 peculiarly coupled with the target materials 24*a* are fixed to a surface of the thin metal film 22 and the sample 24 is inputted to the surface of the thin metal film 22. Accordingly, by analyzing a reflected light reflected from the thin metal film 22, the existence or absence of the target materials 24*a* and the concentration of the target materials 24*a* can be quantitatively detected. Further, in cases where a reflected light from the thin metal film 22 is displayed as a two-dimensional image using a Charge-Coupled Device (CCD), visual observations can be made of a bio reaction at a surface of the thin metal film 22 by virtue of the fact that a portion of the two-dimensional image where the intensity of the reflected light is high is displayed bright and a portion of the two-dimensional image where the intensity of the reflected light is low is displayed dark.

A method for searching new materials by PS-SPCL using the principle of SPR is described with reference to FIGS. 4 to 6 below.

FIG. 4 is a perspective diagram illustrating a PS-SPCL chip in which peptide pools of PS-SPCL are spotted and fixed according to an exemplary embodiment of the present invention.

As shown in FIG. 4, a plurality of peptide pools 33 included in a set of PS-SPCLs are spotted and fixed at predetermined intervals onto a thin metal film 32 formed on a flat type transparent dielectric substrate 31 according to an exemplary embodiment of the present invention. A PS-SPCL chip is the inclusion of the substrate 31 and the thin metal film 32 to which the peptide pools 33 are fixed.

The thin metal film 32 is a metal which supports a surface plasmon phenomenon formed at a predetermined thickness (e.g., a few micrometers). The thin metal film 32 may be formed of metal such as aurum (Au), argentums (Ag) copper (Cu), and aluminum (Al) that emit electron by an external stimulus and have negative dielectric constants. In general, the thin metal film 32 uses argentums (Ag) showing the sharpest SPR peak and aurums (Au) having superior surface stability.

The flat type transparent dielectric substrate 31 serves to support the thin metal film 32. The transparent dielectric substrate 31 is formed of transparent materials to propagate an incident light incident through a prism for exciting SPR to the thin metal film 32. In general, the transparent dielectric substrate 31 can be formed of transparent plastic formed of slide glass and high refractive-index polymer. Also, the transparent dielectric substrate 31 can be formed of polymer materials such as CycloOlefin Copolymer (COC).

Figure 1:
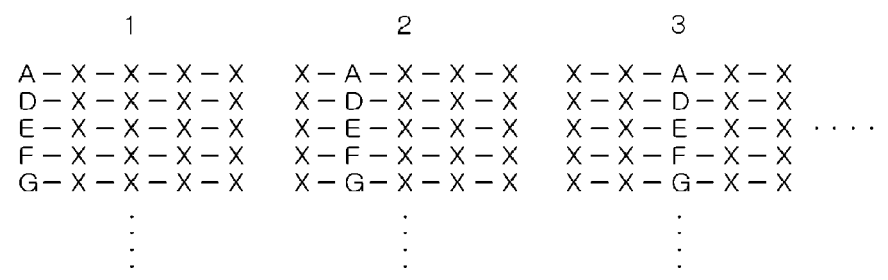

In general, a set of PS-SPCLs consists of a hundred peptide pools. In the peptide pools each, specific amino acids are fixed in specific positions and random amino acids are arrayed in remaining positions. Here, fixed amino acids or fixing positions are different at each peptide pool. That is, as mentioned in FIG. 1, the peptide pools are grouped into a few groups and fixing positions or fixed specific amino acids are the same by group. In peptide pools of the same group, different specific amino acids are fixed in the same position or the same specific amino acids are fixed in different positions.

In the present invention, the peptide pools of a set are spotted at predetermined intervals on the thin metal film 32. In a peptide pool synthesis process, peptides come in contact with the surface of the thin metal film 32 while forming a covalent bond by manipulating N-terminals or C-terminals of the peptides.

For example, in a PS-SPCL synthesis process, the functional group consisting of a hydrogen atom (—SH) is added to the N-terminals or C-terminals and then PS-SPCL is spotted to the thin metal film 32 using general equipment such as a DeoxyriboNucleic Acid (DNA) arrayer. At this time, a surface of the thin metal film 32 reacts with peptides of the spotted PS-SPCL because the surface of the thin metal film 32 has been activated. As a result, the peptides are fixed to the surface of the thin metal film 32 by a covalent bond.

In this exemplary embodiment, a fixing method using a covalent bond is exemplified but this does not intend to limit a method of fixing the peptide pools to the thin metal film 32 in the present invention. The present invention can adopt one of several chemical methods well known to the public.

The fixed PS-SPCL can vary in length from trimer to octamer according to need. Accordingly, spotted peptide pools can be different in number and are not limited particularly in length and number.

Among constituent amino acids of PS-SPCL used for fixing, specific amino acids (e.g., cysteine) can be excluded according to application example. However, this is merely an example but does not intend to limit constituent amino acids of PS-SPCL used in the present invention.

If the peptide pools of the PS-SPCLs are fixed onto the thin metal film 32 as described above, the PS-SPCL chip is installed in an SPR sensor, then specific materials that are targets for analysis are inputted, and then a reflected light obtained is converted into a two-dimensional image by enabling the SPR sensor.

FIG. 5 is a diagram illustrating a state where the PS-SPCL chip is mounted in an SPR sensor to perform PS-SPCL searching using SPR according to an exemplary embodiment of the present invention. That is, FIG. 5 shows the entire scheme of a PS-SPCL searching apparatus using SPR according to an exemplary embodiment of the present invention.

Referring to FIG. 5, the PS-SPCL searching apparatus can include a PS-SPCL chip, an incident light provision unit 45, a prism 41, a reflected light detector 46, and a signal processor 47. The PS-SPCL chip includes a thin metal film 32 and a flat type transparent dielectric substrate 31. The thin metal film 32 spots and fixes one or more peptide pools 33 of PS-SPCL. The flat type transparent dielectric substrate 31 supports the thin metal film 32. The incident light provision unit 45 provides a TM mode incident light for exciting SPR. The prism 41 propagates an incident light provided from the incident light provision unit 45 to an interface between the thin metal film 32 and the flat type transparent dielectric substrate 31 and emits a reflected light reflected from the thin metal film 32. The reflected light detector 46 detects a reflected light emitted through the prism 41 and displays the emitted light as a two-dimensional image.

In more detail, on the prism 41 of the SPR image sensor is disposed the PS-SPCL chip that includes the thin metal film 32 to which the peptide pools 33 each are fixed and the flat type transparent dielectric substrate 31.

Then, target materials 42 of a liquefied state flow on the thin metal film 32 to which the peptide pools 33 of the PS-SPCL are fixed, to induce an interaction between the target materials 42 and the peptide pools 33. Then, a TM polarized incident light 43 is irradiated into the prism 41. Then, a reflected light 44 is emitted from the prism 41 and is detected and processed into a two-dimensional image.

The incident light 43 can be provided from the incident light provision unit 45. The incident light provision unit 45 includes a light source and a polarizer for TM polarizing light generated from the light source. The two-dimensional image can be realized using the reflected light detector 46. The reflected light detector 46 includes a two-dimensional light receiving unit (e.g., a Charge-Coupled Device (CCD) or a Complementary Metal Oxide Semiconductor (CMOS) imaging sensor) and a projection screen or a device for detecting the brightness of each point on a two-dimensional plane.

The TM mode incident light incident on the prism 41 enters the thin metal film 32, thereby exciting SPR on the thin metal film 32.

Because the peptide pools 33 of the PS-SPCL are fixed to the surface of the thin metal film 32, an SPR condition is different in each portion of the thin metal film 32 where the peptide pools 33 are spotted depending on the degree of reaction between the fixed peptide pools 33 and the target materials 42.

In more detail, in cases where light is incident at an SPR angle, at a portion of the thin metal film 32 where coupling with the target materials 42 much occurs, an effective thickness of a surface increases and is far beyond the SPR condition and thus, the intensity of a reflected light increases. On the other hand, at a portion of the thin metal film 32 where coupling with the target materials 42 less occurs, SPR takes place and the energy of the incident light is much propagated to the thin metal film 32 and thus, the intensity of a reflected light decreases.

That is, the intensity of a reflected light reflected from the thin metal film 32 is in inverse proportional to the degree of coupling between the target materials 42 and the peptide pools 33.

Thus, if the reflected light is processed into a two-dimensional image, the reaction of a plurality of the peptide pools 33 can be identified at a time through the fact that a difference of light and darkness takes place in each peptide pool because the intensity of the reflected light is different depending on the degree of coupling of the peptide pools 33. As a result, it can be easily identified that which are optimal amino acids by position.

FIG. 6 is a view showing an example of a two-dimensional image showing the searching result of PS-SPCL searching using SPR according to an exemplary embodiment of the present invention. Here, a vertical axis denotes positions where a specific amino acid is fixed at each row and a horizontal axis denotes a specific amino acid fixed at each column.

Referring to FIG. 6, a different specific amino acid of a peptide pool group of a first row is fixed in a first position of a sequence, a different specific amino acid of a peptide pool group of a second row is fixed in a second position of a sequence, and a different specific amino acid of a peptide pool group of a third row is fixed in a third position of a sequence. Also, it can be noted that an amino acid 'A' is fixed among a peptide pool group of a first column and an amino acid 'D' is fixed among a peptide pool group of a second column.

In the two-dimensional image, the brighter means the larger a coupling force with specific materials. That is, in the two-dimensional image of the reflected light of FIG. 6, it can be noted that 'E' (glutamate) of a first position of a sequence is an optimal amino acid and 'F' (phenylalanine) of a second position of a sequence is an optimal amino acid.

As such, the present invention can obtain information on an optimal amino acid of each position through a single searching work only.

For this, the PS-SPCL searching apparatus of the present invention can further include the signal processor 47 for analyzing a two-dimensional image provided from the reflected light detector 46 and detecting an optimal amino acid in each position.

After searching is completed, the PS-SPCL chip can be reused by removing the target materials 42 inputted to the thin metal film 32 by virtue of a chaotropic reagent such as urea, guanidine hydrochloride or a detergent such as sodium dodecyl sulfate. In more detail, the PS-SPCL chip can be reused through simple physiochemical washing mentioned above because the peptide pools 33 are fixed to the surface of the thin metal film 32 by a covalent bond. The above washing does not certainly intend to limit a physiochemical method for the reuse of the PS-SPCL chip.

While the present invention has been shown and described in connection with the exemplary embodiments, it will be apparent to those skilled in the art that modifications and variations can be made without departing from the spirit and scope of the invention as defined by the appended claims.

The invention claimed is:

1. A Positional Scanning-Synthetic Peptide Combinatorial Library (PS-SPCL) searching method using Surface Plasmon Resonance (SPR), the method comprising:
spotting and fixing each of a plurality of peptide pools to a top surface of a thin metal film;
providing target materials to the top surface of the thin metal film;
providing a Transverse Magnetic (TM) mode light to a bottom surface of the thin metal film and exciting SPR for the thin metal film;
detecting a TM mode reflected light reflected from the thin metal film and displaying the detected light as a two-dimensional image, the two-dimensional image including a plurality of images respectively corresponding to the plurality of peptide pools, each of the plurality of peptide pools including a plurality of peptides, each of the plurality of peptides having a sequence, the plurality of peptide pools including first and second groups of peptide pools, the first group of peptide pools being arranged in a first row and each peptide in the first group having a first one of a plurality of amino acids in a first position, the second group of peptide pools being arranged in a second row and each peptide in the second group having a second one of the plurality of amino acids in a second position, the second position being subsequent to the first position; and
detecting optimal amino acids from the two-dimensional image,
wherein detecting the optimal amino acids includes:
detecting a first peptide pool of the first group of peptide pools that corresponds to a brightest image in the first row; and
determining an amino acid of the detected first peptide pool in the first position as a first one of the optimal amino acids.

2. The method of claim 1, wherein in spotting and fixing each of the plurality of peptide pools to the top surface of the thin metal film, the plurality of peptide pools are fixed to the top surface of the thin metal film by a covalent bond.

3. The method of claim 1, wherein the thin metal film includes a metal that emits electrons by an external stimulus and has a negative dielectric constant.

4. The method of claim 2, further comprising: before spotting and fixing each of the plurality of peptide pools to the top surface of the thin metal film, synthesizing the plurality of peptide pools to cause peptides to contact the top surface of the thin metal film while forming the covalent bond by manipulating N-terminals or C-terminals of the peptides.

5. The method of claim 4, wherein in synthesizing the plurality of peptide pools, a functional group including a —SH is added to the N-terminals or C-terminals.

6. The method of claim 4, wherein in detecting the TM mode reflected light reflected from the thin metal film and displaying the detected light as the two-dimensional image, brightness of each of the plurality of images on a two-dimensional plane is detected through a Charge-Coupled Device (CCD) or a Complementary Metal Oxide Semiconductor (CMOS) image sensor.

7. The method of claim 1, further comprising: after displaying the detected light as the two-dimensional image, removing the target materials provided to the top surface of the thin metal film by a physical or chemical method.

8. The method of claim 7, wherein in removing the target materials by the physical or chemical method, the target materials are removed using a chaotropic reagent or a detergent.

9. The method of claim 8, wherein the chaotropic reagent is urea or guanidine hydrochloride, and the detergent is sodium dodecyl sulfate.

10. The method of claim 1, wherein detecting the optimal amino acids further includes:
detecting a second peptide pool of the second group of peptide pools that corresponds to a brightest image in the second row; and
determining an amino acid of the detected second peptide pool in the second position as a second one of the optimal amino acids.

* * * * *